(12) United States Patent
Shukla et al.

(10) Patent No.: US 6,828,436 B2
(45) Date of Patent: Dec. 7, 2004

(54) METHOD FOR SELECTING A HIGH AFFINITY, LOW MOLECULAR WEIGHT DISPLACER FOR OLIGONUCLEOTIDE PURIFICATION

(75) Inventors: Abhinav A. Shukla, Bothell, WA (US); Ranjit R. Deshmukh, San Diego, CA (US); Steven M. Cramer, Schenectady, NY (US); James A. Moore, Troy, NY (US)

(73) Assignees: ISIS Pharmaceuticals, Inc., Carlsbad, CA (US); Rensselaer Polytechnic Institute, Troy, NY (US)

(*) Notice: Subject to any disclaimer, the term of this patent is extended or adjusted under 35 U.S.C. 154(b) by 0 days.

(21) Appl. No.: 10/146,266

(22) Filed: May 15, 2002

(65) Prior Publication Data

US 2002/0156267 A1 Oct. 24, 2002

Related U.S. Application Data

(63) Continuation of application No. 09/343,006, filed on Jun. 29, 1999, now Pat. No. 6,573,373.

(51) Int. Cl.$^7$ .................... C07H 21/00; C07H 21/02; C07H 21/04
(52) U.S. Cl. ............... 536/25.4; 536/25.41; 536/55.3; 530/416; 530/412; 530/344
(58) Field of Search .................. 530/416, 412, 530/415, 344; 536/25.4, 25.41, 55.3

(56) References Cited

U.S. PATENT DOCUMENTS

| | | | |
|---|---|---|---|
| 5,043,423 A | 8/1991 | Viscomi et al. | 530/344 |
| 5,427,686 A | 6/1995 | Asher | 210/635 |
| 5,439,591 A | 8/1995 | Pliura et al. | 210/635 |
| 5,478,924 A | * 12/1995 | Cramer et al. | 530/416 |
| 5,606,033 A | 2/1997 | Cramer et al. | 530/416 |
| 6,573,373 B1 | * 6/2003 | Shukla et al. | 536/25.4 |

OTHER PUBLICATIONS

Freitag, Nature Biotechnology (1999), vol. 17, pp. 300–302.*

Cramer, S.M. et al., "Ion–Exchange Displacement Chromatography of Proteins," American Chem. Soc., Chromatography Biotech., 1993, Ch. 3, 27–42.

Deshmukh, R.R. et al., "Application of sample displacement techniques to the purification of synthetic oligonucleotides and nucleic acids: a mini–review with experimental results," J. Chromatography A, 1998, 806, 77–92.

Gadam et al., "Characterization of non–linear adsorption properties of dextran–based polyelectrolyte displacers in ion–exchange systems," J. Chromatogr., 1993, 630, 37–52.

Gerstner, J.A. et al., "Gram–scale purification of phosphorothioate oligonucleotides using ion–exchange displacement chromatography," Nucl. Acids Res., 1995, 23(12), 2292–2299.

Gerstner, J.A. et al., "Take another look at displacement chromatography," Chemtech, 1995, 27–32.

Gerstner, J.A. et al., "Rapid ion–exchange displacement chromatography of proteins on perfusive chromatographic supports," J. Chromatography A, 1995, 695, 195–204.

Jayaraman, G. et al., "Ion–exchange displacement chromatography of proteins Dendritic polymers as novel displacers," J. Chromatography A, 1995, 702, 143–155.

Kundu, A. et al., "Low–Molecular–Weight Displacers for High–Resolution Protein Separations," Anal. Biochem., 1997, 248, 111–116.

Kundu, A. et al., "Protected Amino Acids as Novel Low–Molecular–Weight Displacers in Cation–Exchange Displacement Chromatography," Biotech. Bioengineer., 1995, 48, 452–460.

Kundu, A. et al., "Displacement Chromatography of Proteins Using Sucrose Octasulfate,", BioPharm., 1997, 64–68, 70, and 95.

Kundu et al., "Antibiotics as low–molecular–mass displacers in ion–exchange displacement chromatography," J. Chromatography A, 1995, 707, 57–67.

Patrickios, C.S. et al., "Chromatographic Characterization of Acrylic Polyampholytes," American Chem. Soc., Chromatography Biotech., 1994, Ch. 4, 144–153.

Shukla, A.A. et al., "Structural characteristics of low–molecular–mass displacers for cationn–exchange chromatography," J. Chromatography A, 1998, 814, 83–95.

Shukla, A.A. et al., "Purification of an Antigenic Vaccine protein by Selective Displacement Chromatography," Biotechnol. Prog., 1998, 14, 92–101.

Shukla et al., "Synthesis and Characterization of High–Affinity, Low Molecular Weight Displacers for Cation–Exchange Chromatography," Ind. Eng. Chem. Res., 1998, 37, 4090–4098.

Horvath, C., et al., "Operating parameters in high–performance displacement chromatography," J. Chromatography, 1983, 255, 273–279.

Rassi, et al., "High–performance displacement chromatography of nucleic acid fragments in a tandem enzyme reactor–liquid chromatography system," J. Chromatography, 1983, 266, 319–340.

\* cited by examiner

*Primary Examiner*—James O. Wilson
*Assistant Examiner*—Patrick T. Lewis
(74) *Attorney, Agent, or Firm*—Woodcock Washburn LLP

(57) ABSTRACT

A method for purifying oligonucleotides by displacement chromatography on anion-exchange media, using high affinity, low molecular weight (less than about 10000 Da) displacers, is disclosed. Several examples of high affinity, low molecular weight anionic displacers are provided, including polycyclic aromatic compounds having sulfonic acid moieties attached thereon. The efficacy of the technique for high resolution separation of oligonucleotides is demonstrated for an industrial mixture.

4 Claims, 15 Drawing Sheets

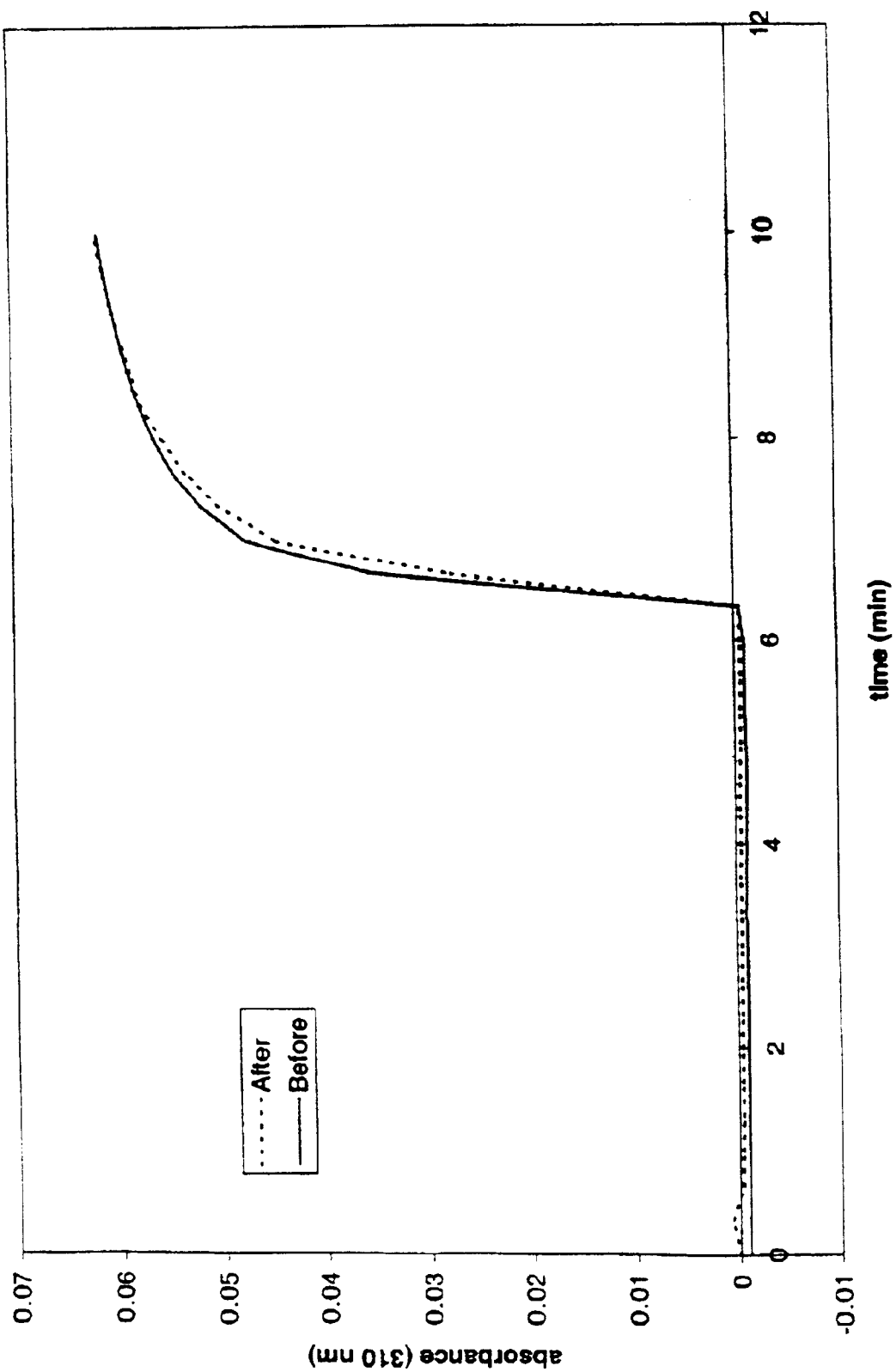

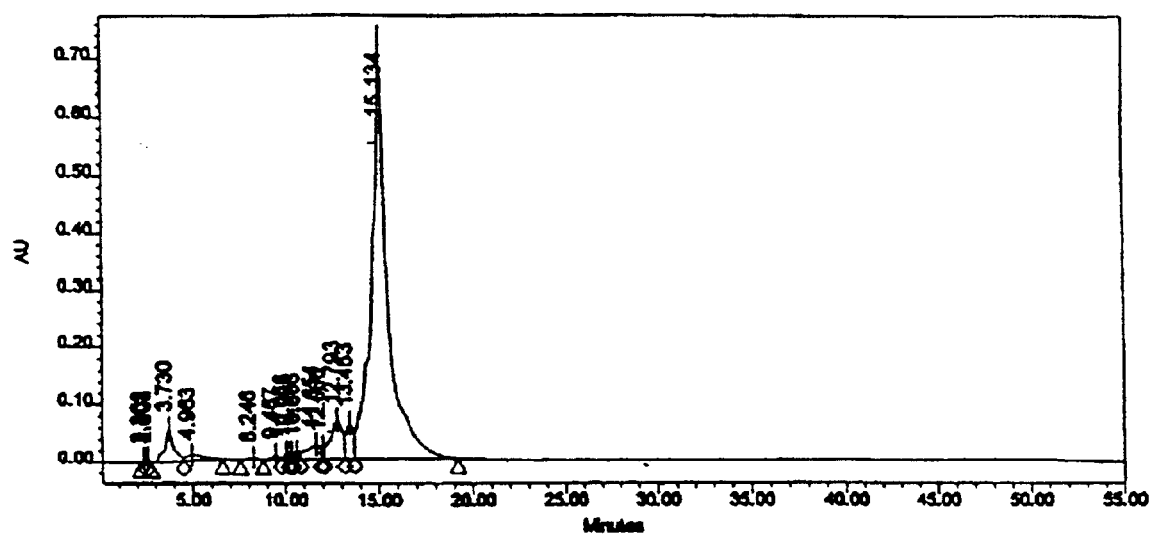

METHOD FOR SELECTING A HIGH AFFINITY, LOW MOLECULAR WEIGHT DISPLACER FOR OLIGONUCLEOTIDE PURIFICATION

This application is a continuation of Ser. No. 09/343,006, filed Jun. 29, 1999, which was issued as U.S. Pat. No. 6,573,373 on Jun. 3, 2003, the entirety of which is incorporated herein by reference.

STATEMENT AS TO POSSIBLE RIGHTS UNDER FEDERALLY SPONSORED RESEARCH

This invention was made with support from the National Institute of Health under Grant No. GM47372. The United States Government may have rights in the invention.

FIELD OF THE INVENTION

The present invention relates to displacement chromatography of oligonucleotides using low molecular weight, high affinity anionic displacers.

BACKGROUND OF THE INVENTION

Oligonucleotides have generated significant interest as drug candidates for a wide variety of diseases, in particular as antisense therapeutics and as potent antibiotics. Several antisense oligonucleotide drugs are currently undergoing human clinical trials, and many others are in a preclinical phase.

Oligonucleotides are single strands of nucleic acids with DNA or RNA bases, ranging in length from two to 50 bases or nucleotides. Phosphorothicate derivatives of oligonucleotides have also been utilized because of their higher in vivo stability compared to the parent phosphodiester compounds. In the phosphorothioate derivatives, a non-bridging oxygen atom in the phosphodiester backbone is replaced with a sulfur atom. This substitution enhances nuclease resistance and thus, in vivo stability.

Solid-phase synthesis methods are now available for large-scale preparation of oligonucleotides. Solid-state synthesis of an oligonucleotide results in a crude product containing not only the desired full-length (n-length or n-mer) oligonucleotide, but also multiple, closely-related deletion or "failure sequences," primarily of length n-1. These so-called failure sequences arise by failure to add a base at the necessary position. Such failures or deletions can arise at multiple positions along the chain. Multiple failure sequences, of length (n-1, n-2, n-x), are also present for any given length. In addition, (n+1)mers may be present. Therefore, purification methods that operate on a preparative scale are needed.

Chromatographic preparation and purification of oligonucleotides can potentially provide the necessary scale and purity, but can also present unique challenges. First, oligonucleotides exhibit an extremely high binding affinity for anion-exchange chromatographic resins as compared to molecules typically encountered in biopharmaceutical purification (for example, proteins). Second, the failure sequences present are so closely-related to the desired product that the components are difficult to separate. Finally, oligonucleotides exhibit several centers of isomerism leading to the possibility of considerable heterogeneity of the mixtures of product and failure sequences.

A chromatographic system can be operated in one of two major modes, elution (including linear gradient, step gradient, and isocratic elution) or displacement. The two modes may be distinguished both in theory and in practice. In elution chromatography, a solution of the sample to be purified is applied to a stationary phase, commonly in a column. A mobile phase is chosen such that the sample is neither irreversibly adsorbed nor totally unadsorbed, but rather binds reversibly. As the mobile phase is caused to flow over the stationary phase, an equilibrium is established between the mobile phase and the stationary phase whereby components of the sample pass along the column at speeds which reflects their affinity for the stationary phase relative to the other components that may occur in the original sample. The differential migration process is outlined schematically in FIG. 1, and a typical chromatogram is shown in FIG. 2. Of particular note is the fact that the eluting solvent front, or zero column volume in isocratic elution, always precedes the sample off the column.

A modification and extension of isocratic elution chromatography is found in step gradient chromatography wherein a series of eluants of varying composition are passed over the stationary phase.

In ion-exchange chromatography, step changes in the mobile phase salt concentration and/or pH are employed to elute or desorb materials such as, for example, proteins.

A schematic illustrating the operation of a chromatographic system in displacement mode is shown in FIG. 3. The column is initially equilibrated with a buffer in which most of the components to be separated have a relatively high affinity for the stationary phase. Following the equilibration step, a feed mixture containing the components to be separated is introduced into the column and is then followed by a constant infusion of the displacer solution. A displacer is selected such that it has a higher affinity for the stationary phase than any of the feed components. As a result, the displacer can effectively drive the feed components off the column ahead of its front. Under appropriate conditions, the displacer induces the feed components to develop into adjacent "squarewave" zones of highly concentrated, often pure material. The displacer emerges from the column following the zones of purified components. After the breakthrough of the displacer with the column effluent, the column is regenerated and is ready for another cycle.

An important distinction between displacement chromatography and elution chromatography is that in elution chromatography, desorbents, including salts for ion-exchange chromatography, move through the feed zones, while in displacement chromatography, the displacer front always remains behind the adjacent feed zones in the displacement train. This distinction is important because relatively large separation factors are generally required to achieve satisfactory resolution in elution chromatography, while displacement chromatography can potentially purify components from mixtures having low separation factors.

A key operational feature which distinguishes displacement chromatography from elution chromatography is the use of a displacer molecule. In elution chromatography, the eluant usually has a lower affinity for the stationary phase than any of the components in the mixture to be separated, whereas in displacement chromatography, the eluant, which is the displacer, has a higher affinity.

Displacement chromatography has some particularly advantageous characteristics for process scale chromatography of biological macromolecules such as oligonucleotides. First, displacement chromatography can concentrate components from mixtures. By comparison, isocratic elution chromatography results in product dilution during separation. Second, displacement chromatography can achieve product separation and concentration in a single step. Further, since the displacement process operates in the nonlinear region of the equilibrium isotherm, high column loadings are possible. This allows for improved column utilization compared to elution chromatography. Furthermore, displacement chromatography can purify components from mixtures having low separation factors, while relatively large separation factors are required for satisfactory resolution in desorption chromatography.

Preparative ion-exchange chromatography operated in the displacement mode is, therefore, a potentially attractive method for purifying oligonucleotides because of the high resolution and high throughput that can be obtained. However, displacement chromatography, as it is traditionally known, has a number of drawbacks compared to elution chromatography for the purification of oligonucleotides. Two of the major problems are difficulty in regeneration of the column and the presence of displacer in some of the purified fractions.

Since the displacement process uses a high affinity compound as the displacer, the time for regeneration and re-equilibration can be long compared to elution chromatography. The second problem, that of contamination by the displacer, has arisen because a common characteristic of displacers used in ion-exchange systems has been their relatively high molecular weight. Heretofore the art has taught the use of high molecular weight polyelectrolyte displacers on the assumption that it is necessary to have a large polyelectrolyte in order to ensure a higher binding coefficient than the biomolecule that is to be displaced. The rationale behind such an assumption is that the binding of a molecule to an adsorbent surface of an ion-exchange stationary phase is related only to its characteristic charge. Characteristic charge is the average number of sites of interaction of a solute with a stationary phase. High molecular weight displacers exhibit both of the disadvantages enumerated above: they bind tightly to the stationary phase and, therefore, require stringent conditions for regenerating the column, and traces of the displacer that may contaminate the product fraction are difficult to remove.

Low molecular weight displacers for protein separation that do not require extensive regeneration of the column and that can be readily removed from the product have been described by Cramer et al. (U.S. Pat. No. 5,606,033, issued Feb. 25, 1997; U.S. Pat. No. 5,478,924, issued Dec. 26, 1995). However, while the low molecular weight displacers identified so far have been successful in displacing moderately bound biomolecules such as proteins, they have been unsuccessful in displacing very highly retained compounds in ion-exchange systems, for example, oligonucleotides. Prior art disclosures relating to purification of oligonucleotides in ion-exchange systems have described only the use of relatively large polyelectrolytes (>40,000 Daltons) as displacers. For example, use of displacement chromatography with a high molecular weight polyelectrolyte displacer, a sulfonated polysaccharide, for the purification of oligonucleotides has been reported by Gerstner et al. (*J. Nucl. Acids Res.* 1995, 23, 2292–2299).

Therefore, there is a need for a separation process of oligonucleotides having the advantages of displacement chromatography (high resolution and high throughput) while avoiding the disadvantages (difficult column regeneration and contamination of the product with the displacer.)

SUMMARY OF THE INVENTION

In one aspect, the present invention relates to methods for purifying an oligonucleotide, or several oligonucleotides, comprising:

(a) loading said oligonucleotide onto an anion-exchange column having a stationary phase; and (b) displacing said oligonucleotide from said anion-exchange column by an anionic displacer having a molecular weight of less than about 10,000, said anionic displacer having a higher affinity for said stationary phase of said anion-exchange column than said oligonucleotide.

Preferably, the molecular weight of the displacer is less than about 5,000. More preferably, the molecular weight of the displacer is less than about 2,500.

A preferred composition for the displacer is a substituted or unsubstituted aromatic compound having at least one anionic substituent. Another preferred composition for the displacer is a substituted or unsubstituted aliphatic compound having at least one anionic substituent. Preferred anionic substitutents are sulfate, sulfonate, phosphate, phosphonate and carboxylate groups. More preferred anionic substitutents are sulfonate groups. A preferred aromatic compound is a substituted or unsubstituted polycyclic aromatic compound having at least one anionic substituent. Preferred polycyclic aromatic sulfonates are amaranth and calcion.

BRIEF DESCRIPTION OF THE DRAWINGS

FIG. 8 shows an HPLC chromatogram illustrating the effective regeneration of the column used in FIG. 5 (Example 2).

FIG. 9*a* is an analytical capillary gel electropherogram of the crude phosphodiester 20 mer SEQ ID NO. 1 (ISIS-2302) containing several lower retained impurities which appear as shoulders on the main product peak (Example 3).

DETAILED DESCRIPTION OF PREFERRED EMBODIMENTS

Figure 1:
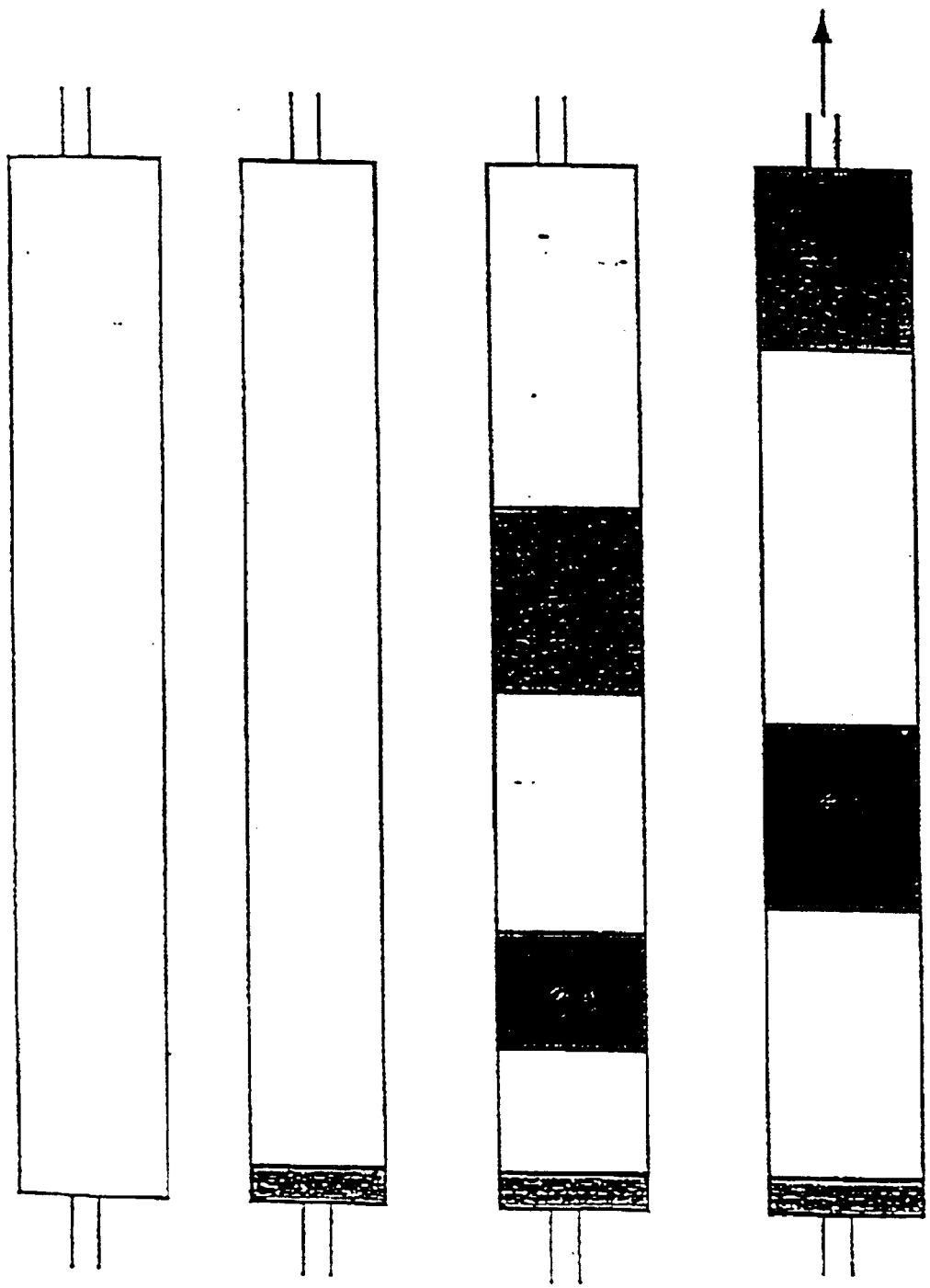
FIG. 1 is a schematic representation of isocratic linear elution chromatography as typically practiced.
Figure 2:
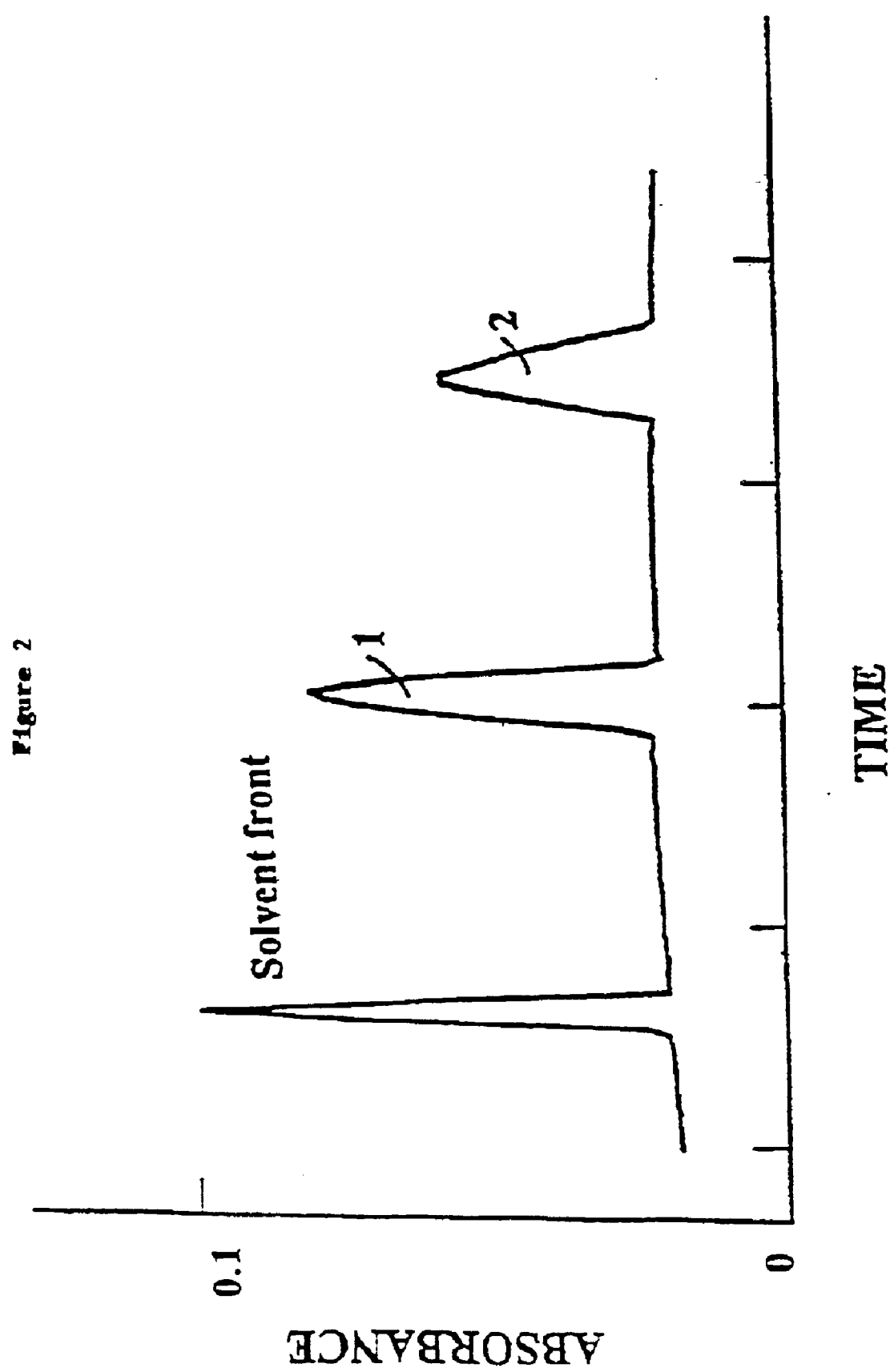
FIG. 2 is a typical HPLC elution chromatogram.
Figure 3:
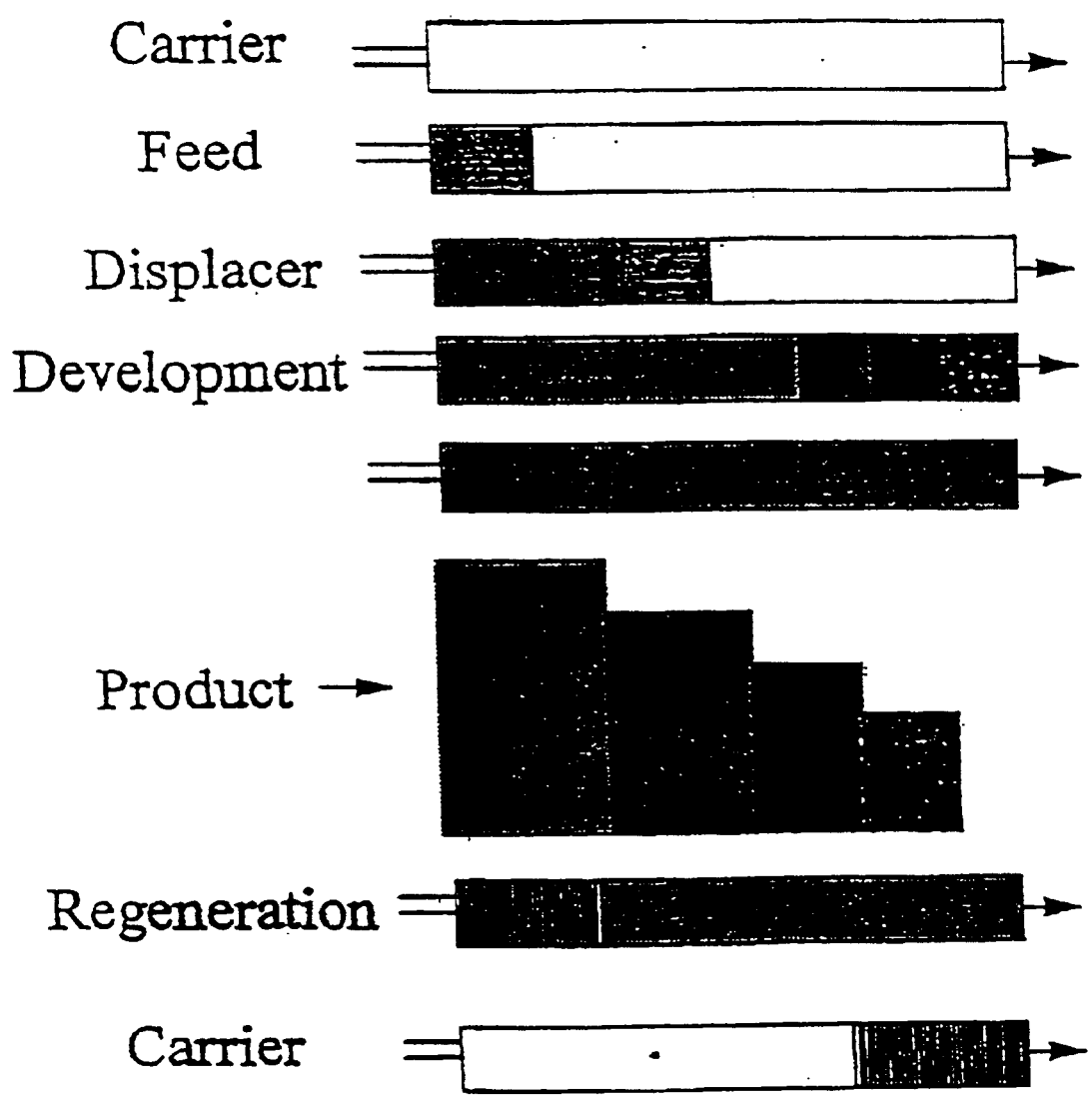
FIG. 3 is a schematic representation of displacement chromatography.

The method of the present invention relates to separation and purification of oligonucleotides by ion-exchange chromatography operated in the displacement mode. A low molecular weight anionic displacer having higher affinity for the stationary phase than the oligonucleotides to be separated or purified is utilized. The oligonucleotide to be purified is dissolved in a solvent and loaded onto an anion-exchange column having a stationary phase. The oligonucleotide is eluted with an anionic displacer which displaces the oligonucleotide from the anion-exchange column.

In the context of the present invention, low molecular weight means a molecular weight of less than 10,000. Preferably, a displacer used in the method of the present invention has a molecular weight of less than 5,000. More preferably, the displacer has a molecular weight of less than 2,500.

Affinity of the displacer for the stationary phase of the chromatographic system relative to the oligonucleotides to be separated or purified is defined with reference to an improved mathematical model for displacement chromatography: Steric Mass Action (SMA) ion-exchange model. The SMA ion-exchange model is capable of predicting complex behavior in ion-exchange systems. This model has three solute parameters: characteristic charge ν is the number of salt counterions displaced by the solute when it binds to the stationary phase surface; steric factor σ is the number of salt counterion sites on the surface which are shielded by the adsorbed solute and hence unavailable for exchange with any other solute molecules; and equilibrium constant κ is that for the exchange reaction between the salt counterions and the solute.

According to the SMA model, the governing parameter that regulates the ability of one solute to displace another is dynamic affinity. Dynamic affinity is defined as:

$$\lambda = \left(\frac{K}{\Delta}\right)^{\frac{1}{\nu}}$$

wherein λ is the dynamic affinity, Δ is the displacer partition ratio, and κ and ν are as defined above. Δ is equal to $Q_d/C_d$, where $Q_d$ and $C_d$ are the displacer concentrations in the stationary phase and mobile phase, respectively. The value of parameter Δ varies with the operating conditions for the displacement, which include the concentrations of displacer and salt.

Affinity of the displacer for the stationary phase of an anion-exchange system higher than that of the oligonucleotides to be separated or purified for the same stationary phase is defined with reference to the SMA model. Higher affinity means that the displacer has a greater dynamic affinity λ than that of the oligonucleotides. Dynamic affinity of the displacer and the oligonucleotides can be readily determined by constructing a plot of log κ versus ν for the displacer and oligonucleotides. This is called a dynamic affinity plot. The slope of the line is the dynamic affinity λ of the compound or mixture of compounds. Where the line for the displacer falls above or counterclockwise from the line for the oligonucleotides, the displacer has higher affinity for the stationary phase under those operating conditions than does the oligonucleotide or mixture of oligonucleotides. The plot is, therefore, used to determine the ability of a displacer to displace a given oligonucleotide under the operating conditions for the displacement.

Figure 4:
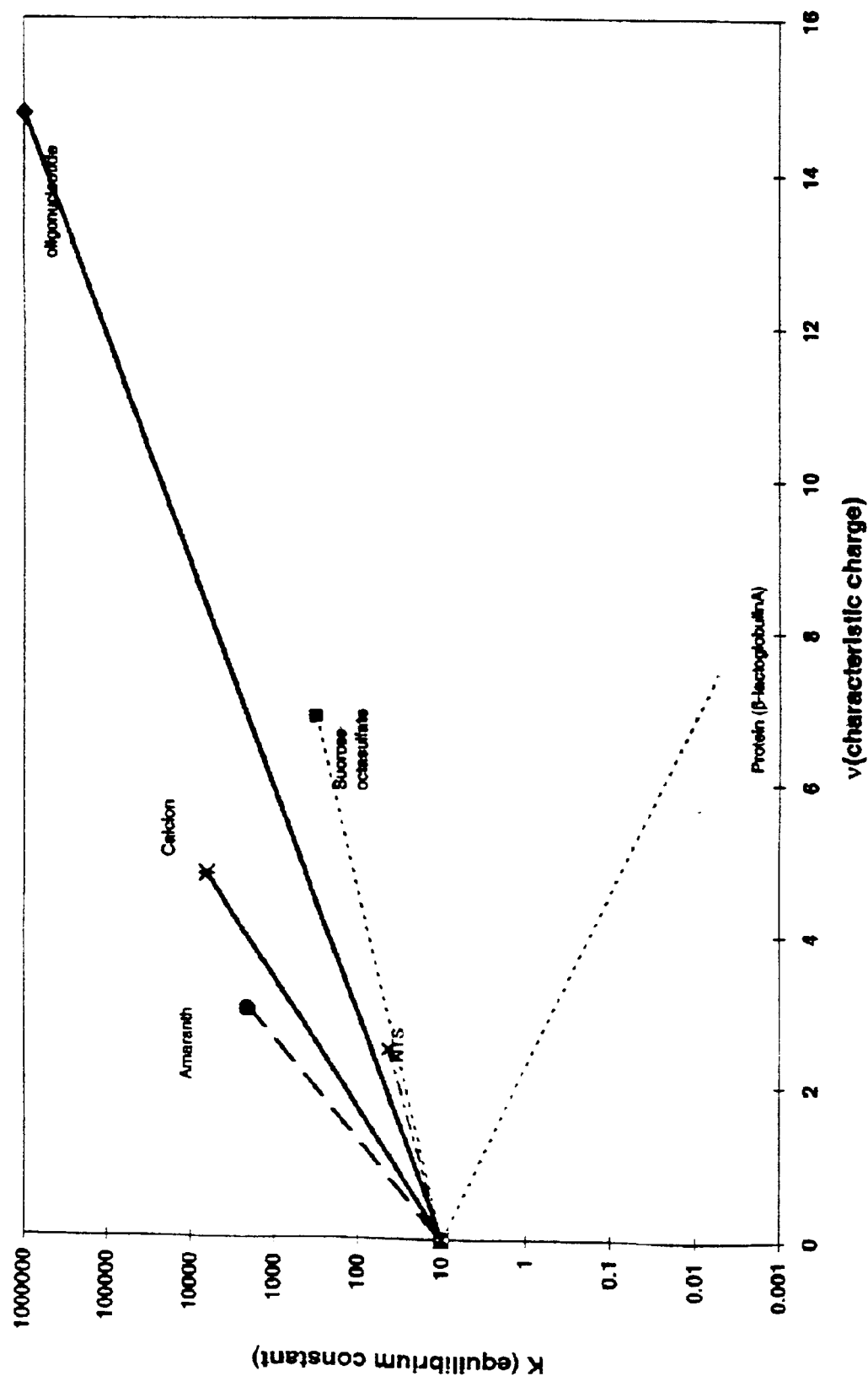
FIG. 4 is a dynamic-affinity plot for three displacers, a typical 20 mer phosphorothioate oligonucleotide (SEQ ID NO. 2, ISIS-2105), and a protein.

An exemplary dynamic affinity plot is shown in FIG. 4. The values of log κ and ν are plotted for a typical phosphorothioate antisense oligonucleotide, a typical protein and several potential displacers. Viewed in a counterclockwise direction, that is, in order of increasing slopes, starting with the line for a typical protein, this plot shows increasing affinity of the solutes under the experimental conditions. It is evident that even the highest affinity low molecular weight displacer previously identified for anion-exchange, sucrose octasulfate, did not possess enough affinity to displace this oligonucleotide. In fact, the oligonucleotide has an equilibrium constant that is several orders of magnitude higher than that of a typical anionic protein, β-lactoglobulin A, as shown in FIG. 4.

The three SMA parameters, ν, σ, and κ, may be determined experimentally. The characteristic charge and equilibrium constant of the oligonucleotides to be purified may be determined using linear gradient elution retention data with different slopes of the linear gradient (Shukla et al., *Ind. Eng. Chem. Res.*, 1998, 37, 4090–4098, which is herein incorporated by reference). The steric factor of the oligonucleotides may then be determined from the capacities obtained from frontal experiments at two or more displacer concentrations (Gadam et al, *J. Chromatogr.*, 1993, 630, 37–52), which is herein incorporated by reference). The magnitude of the induced gradient obtained during these frontal experiments can provide an independent measure for the characteristic charge ν.

A slightly different procedure may also be employed to obtain the SMA parameters of the displacer. Isocratic experiments may be conducted at different mobile phase salt concentrations, and a plot of log k' vs. log (salt concentration), where k' is the dimensionless retention time of a solute at a specific mobile phase salt concentration, may be made. The values of the slope and intercept of the line are used to calculate the characteristic charge ν and the equilibrium constant κ, respectively (Gadam et al., *J. Chromatogr.*, 1993, 630, 37–52). The frontal experiments described above may be used to determine the steric factor and an independent measure of ν.

The retention process in ion-exchange is not solely determined by electrostatic interactions but may be greatly enhanced by non-specific interactions. One of the dominant factors which can play a major role in governing retention on an anion-exchange resin are hydrophobic interactions. For example, aromatic compounds having multiple sulfonic acid functionalities may be effective displacers for oligonucleotides.

Therefore, an anionic displacer having higher affinity for a stationary phase of an anion-exchange system may be an aromatic, substituted aromatic aliphatic or substituted aliphatic compound containing at least one anionic substituent. Preferred anionic substituents are sulfate, sulfonate, phosphate, phosphonate and carboxylate groups. More preferred is a substituted or unsubstituted aromatic anionic displacer containing at least one sulfonate group. The anionic displacer may also be a polycyclic aromatic or substituted polycyclic aromatic compound containing at least one anionic substituent. Preferred anionic substituents are sulfate, sulfonate, phosphate, phosphonate and carboxylate groups. A preferred substituted or unsubstituted polycyclic aromatic anionic displacer contains at least one sulfonate group. Examples of polycyclic aromatic sulfonate displacers having higher affinity for a stationary phase than an oligonucleotide are amaranth (I) and calcion (II), both available from Aldrich Chemical Company. The structures of I and II are shown below.

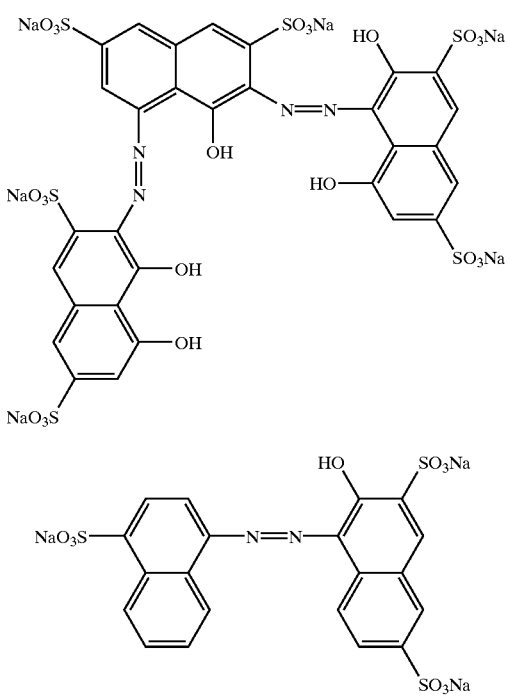

Other exemplary aromatic sulfonates which may exhibit higher affinity for a stationary phase of an anion-exchange system than an oligonucleotide to be purified under the operating conditions of the system are New Coccine, Ponceau S, Ponceau SS, Hydroxy Naphthol Blue, Brilliant Black, Anthraquinone Disulfonic Acid, Potassium Indigotetrasulfonate, Sulfazo III, Reactive Orange 16, Acid Alizarin Violet N, Acid Black 24, Acid Blue 29, Acid Blue 80, Acid Blue 92, Acid Blue 113, Acid Blue 120, Acid Green 25, Acid Green 27, Acid Orange 8, Acid Orange 51, Acid Orange 63, Acid Orange 74, Acid Red 1, Acid Red 4, Acid Red 8, Acid Red 97, Acid Red 106, Acid Red 114, Acid Red 151, Acid Red183, Acid Violet 5, Acid Violet 7, Acid Yellow 17, Acid Yellow 25, Acid Yellow 29, Acid Yellow 34, Acid Yellow 38, Acid Yellow 40, Acid Yellow 42, Acid Yellow 65, Acid Yellow 76, and Acid Yellow 99. All of these compounds are commercially available from Aldrich Chemical Company.

The method of the present invention may be used with conventional anion-exchange systems and conventional displacement chromatography procedures. An example of a useful anion-exchange column is a Poros HQ/M column, which has a stationary phase composed of a rigid polystyrene-divinylbenzene bead covered with a hydrophilic layer. The column is available from PerSeptive Biosystems, Inc. Displacement chromatography operations are typically carried out by initially equilibrating the column with carrier solution and then sequentially perfusing with feed, displacer, and regenerant solutions. The feed and the displacer solutions are commonly prepared in the same buffer solution as the carrier.

As used herein, the term oligonucleotide includes oligomers containing two or more nucleoside subunits having phosphorus internucleoside linking moieties. Nucleoside subunits according to the invention have a ribofuranose moiety attached to a nucleobase through a glycosyl bond. oligonucleotides according to the present invention preferably comprise from about 5 to about 50 nucleosides. It is more preferred that such compounds comprise from about 8 to about 30 nucleosides. It is most preferred that such compounds comprise from about 15 to about 25 nucleosides.

Additional objects, advantages, and novel features of the present invention will become apparent to those skilled in the art upon examination of the following examples. The following examples illustrate the invention and are not intended to limit the same. Those skilled in the art will recognize, or be able to ascertain through routine experimentation, numerous equivalents to the specific substances, compositions, and procedures described herein. Such equivalents are considered to be within the scope of the present invention.

EXAMPLES

Example 1

Displacement Chromatography of a Phosphorothioate 20 mer, SEQ ID NO: 1 (ISIS-2302) GCC CAA GCT GGC ATC CGT CA (P=S)

FIG. 4 shows a Dynamic Affinity plot for preferred displacers for a typical phosphorothioate oligonucleotide, amaranth (I) and calcion (II), in comparison to a disaccharide bearing eight sulfate groups, sucrose octasulfate. The line for sucrose octasulfate falls below that of the oligonucleotide, while those for amaranth and calcion fall counterclockwise (above) to that of the oligonucleotide. Therefore, both amaranth and calcion have higher affinity for the stationary phase than the oligonucleotide.

Figure 5:
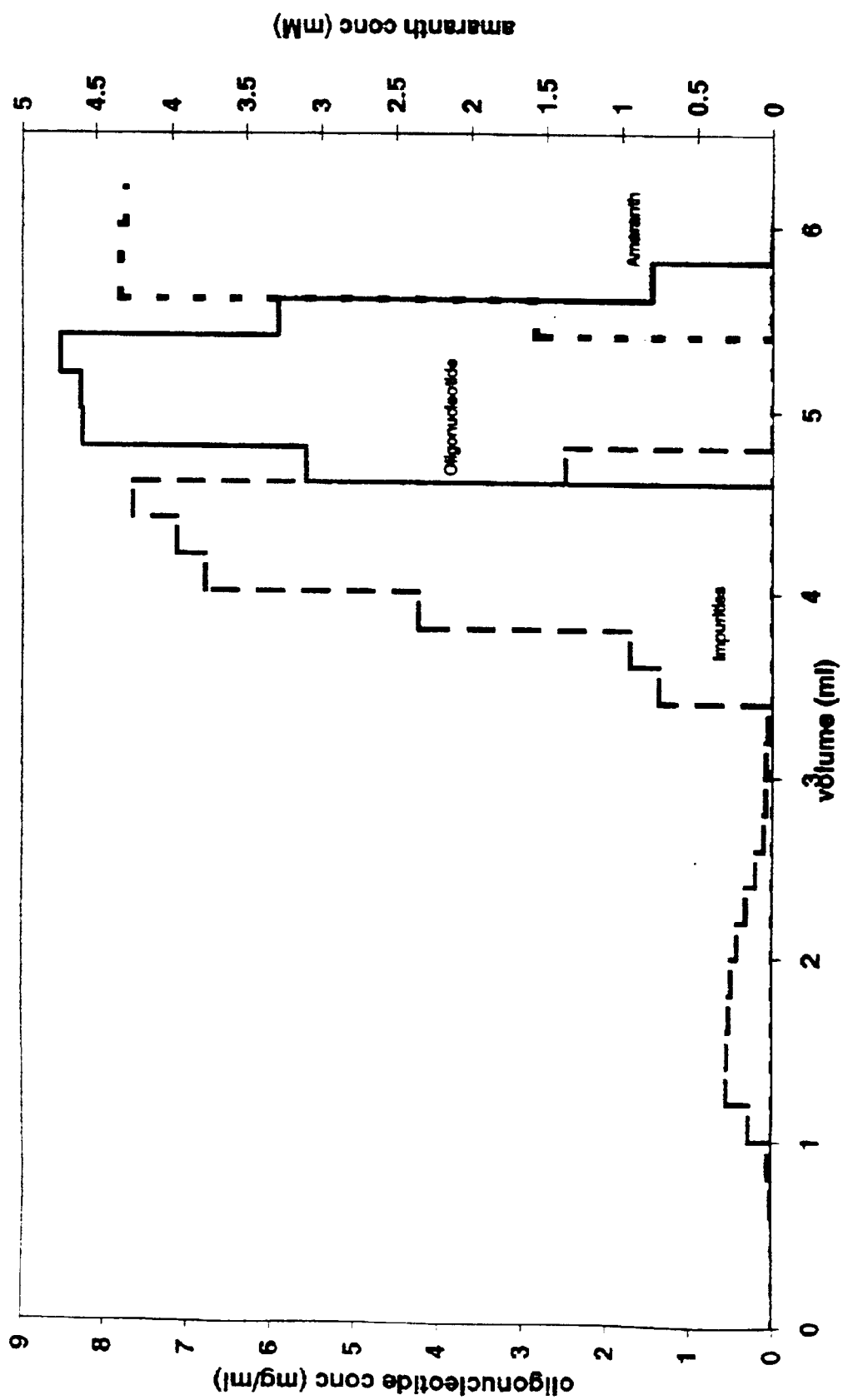
FIG. 5 is a displacement chromatogram for SEQ ID NO. 1 (ISIS-2302) purified using amaranth as the displacer (Example 1).

The ability of the dynamic affinity parameter to predict real-world behavior was confirmed for amaranth in a separation of a typical phosphorothioate oligonucleotide. FIG. 5 shows a histogram of a displacement separation of SEQ ID NO: 1, a 20-mer phosphorothioate antisense oligonucleotide, using amaranth as a displacer on a Poros HQ/M column (4.6×100 mm I.D., 20 μm particles), at a flow rate of 0.2 mL/min. The carrier solution and mobile phase was a 20 mM NaOH/500 mM NaCl solution. The feed and displacer solution were prepared from the carrier solution and the feed consisted of 11.98 mg oligonucleotide. An effective displacement was demonstrated with a sharp boundary between zones containing the impurities and the desired oligonucleotide, and between zones containing the oligonucleotide and the amaranth displacer. Thus, the histogram demonstrates the resolving power of amaranth in displacement chromatography of oligonucleotides.

Figure 6A:
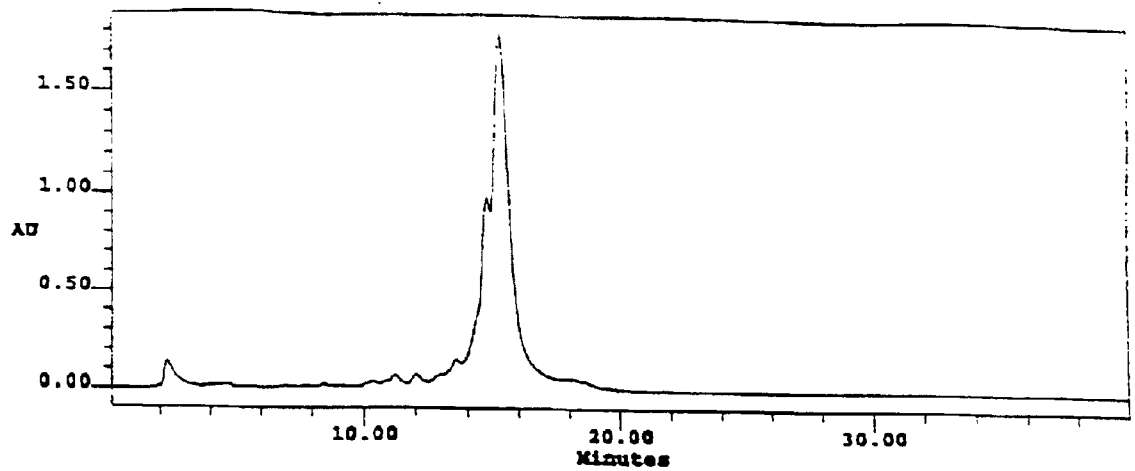
FIG. 6*a* is an analytical anion-exchange chromatogram of the oligonucleotide feed shown in FIG. 5.
Figure 6B:
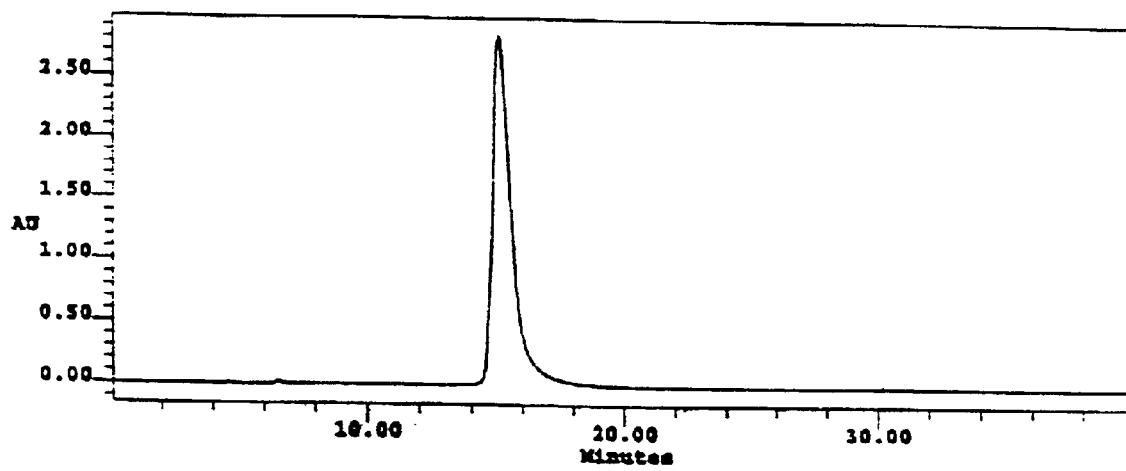
FIG. 6*b* is an analytical anion-exchange chromatogram of one of the purified fractions from the displacement shown in FIG. 5.
Figure 7A:
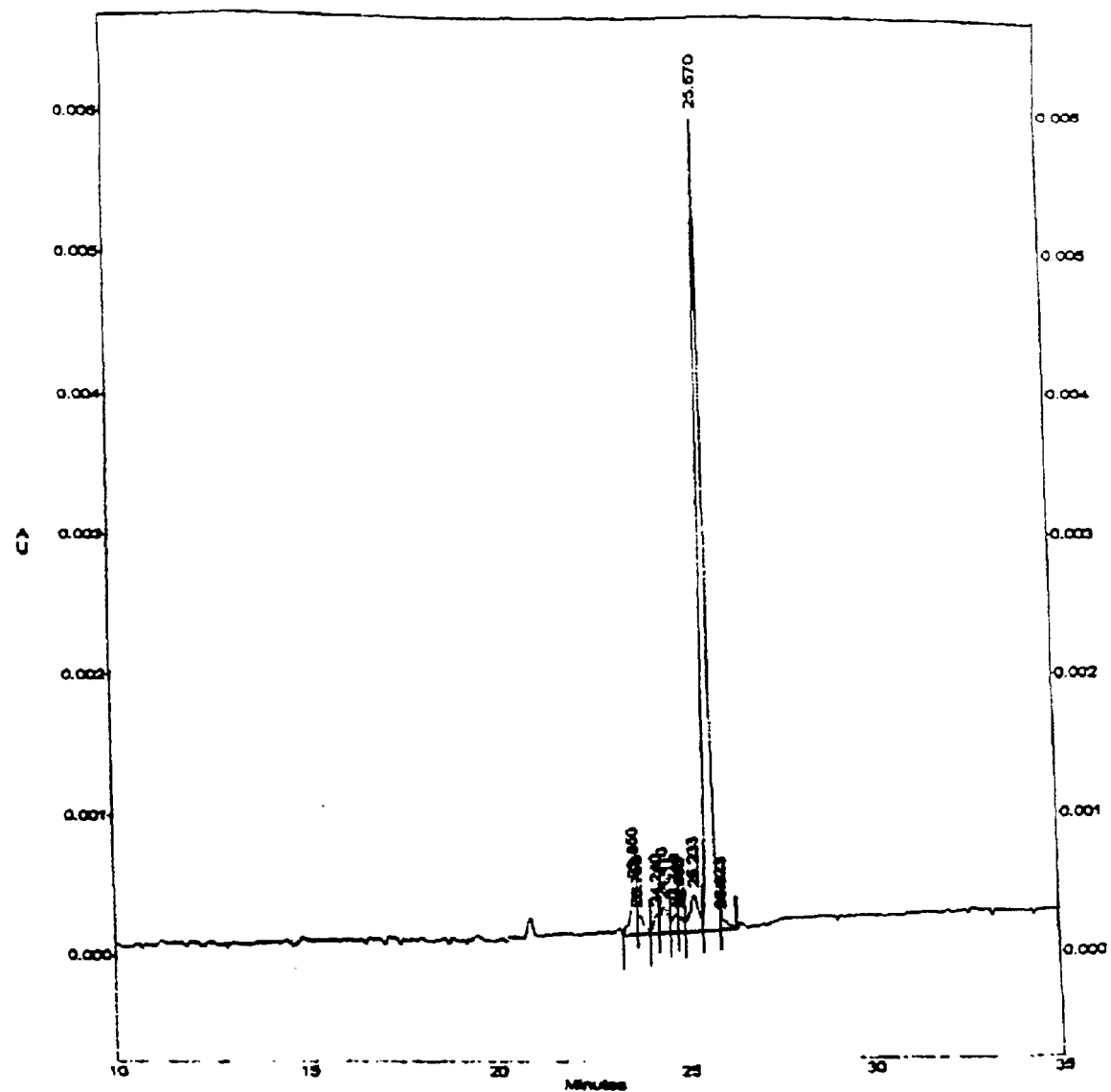
FIG. 7*a* is an analytical capillary gel electropherogram of the feed from the displacement of the oligonucleotide in FIG. 5.
Figure 7B:
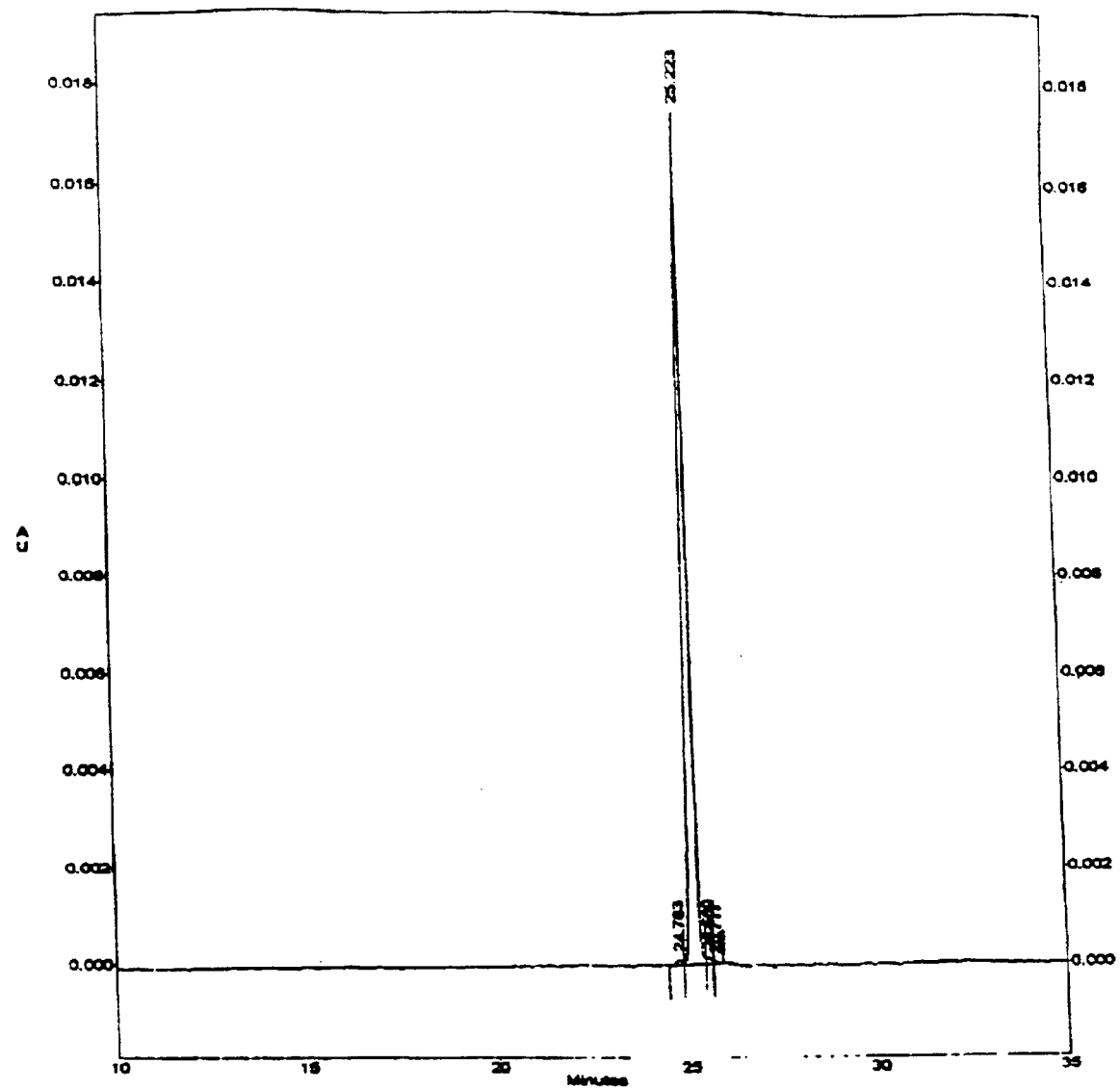
FIG. 7*b* is an analytical capillary gel electropherogram of the purified pool from displacement of the oligonucleotide in FIG. 5.

High temperature anion-exchange analysis of the feed and of the fraction containing the desired oligonucleotide confirmed the purity of the product oligonucleotide. Chromatograms from the displacement experiment show the oligonucleotide fraction collected (FIG. 6a) and the feed component from the displacement experiment (FIG. 6b). Even though the feed was only about 58% pure, the oligonucleotide fraction had a purity of about 99% by anion-exchange analysis. Capillary electropherograms for the feed and product pool from the example in FIG. 5 are shown in FIGS. 7a and 7b.

The displacement histogram depicted in FIG. 5 was prepared using the separation parameters listed above and the general procedure illustrated below. One fractions per minute was collected and analyzed by analytical anion-exchange assay to determine the concentration of the components and their purities. Standard curves for the peak area versus the oligonucleotide concentration and the peak area versus the displacer concentration were generated using the sample of pure oligonucleotide and a sample of known concentration for the displacer, respectively. The concentration of oligonucleotide and amaranth in each of the fractions was then determined by using this standard curve to calculate a value of the extinction coefficient (peak area per unit concentration). The same extinction coefficient was assumed for the mono-phosphodiester (P=O)1 component and other impurity species since these are chemically very similar. For these experiments the cumulative impurity concentration was determined by subtracting the main peak, i.e. the all phosphorothioate (P=S) parent peak, concentration from the total oligonucleotide concentration in each fraction. A histogram was generated to represent this experimental data by plotting the cumulative concentration of impurities, product oligonucleotide and amaranth for each of the fractions vs. volume of column effluent.

Example 2

Column Regeneration Following Displacement Chromatography

Following purification of the phosphorothioate oligonucleotide in Example 1 above the column was regenerated. Demonstrating effective regeneration of the stationary phase after a displacement run is important to enable the use of a compound as an efficient displacer. FIG. 8 shows an HPLC chromatogram with the breakthrough curves for nitrate ions before and after the column had been put through several successive displacement steps as illustrated in Example 1. As can be seen, the breakthrough curves overlay each other signifying an effective column regeneration using standard protocols. The 4 step regeneration protocol is shown below.

1) Elute column with 5 column volumes of 2.5 M NaCl and 20 mM NaOH.
2) Elute column with 5 column volumes water.
3) Elute column with 5 column volumes 25% v/v acetonitrile and 20 mM NaOH.
4) Elute column with 5 column volumes water.

Example 3
Displacement Chromatography of a Phosphodiester 20 mer, SEQ ID NO: 1 (ISIS-2302) GCC CAA GCT GGC ATC CGT CA (P=O)

Figure 9B:
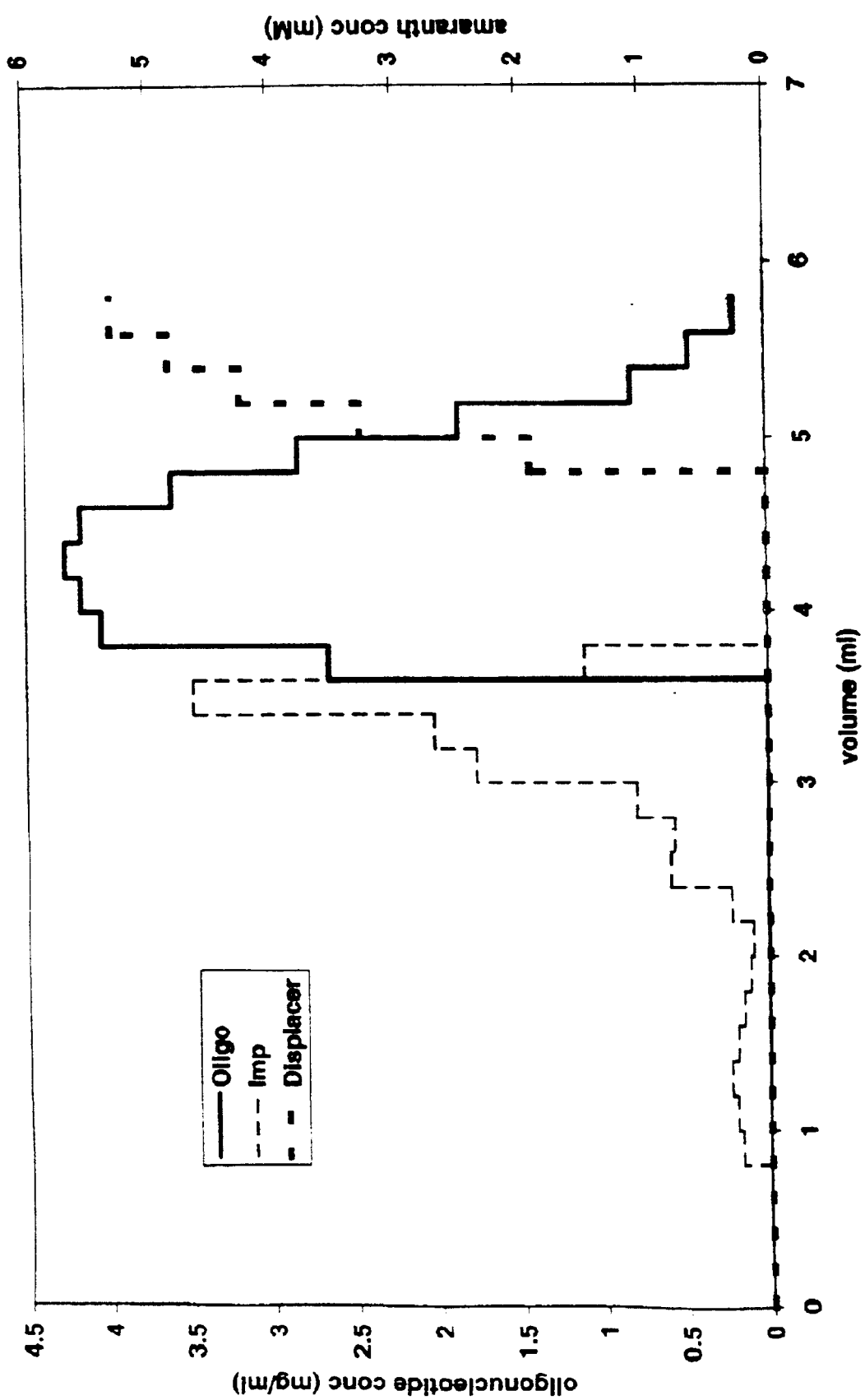
FIG. 9*b* is a displacement chromatogram for the phosphodiester illustrated in FIG. 9*a*.
Figure 9C:
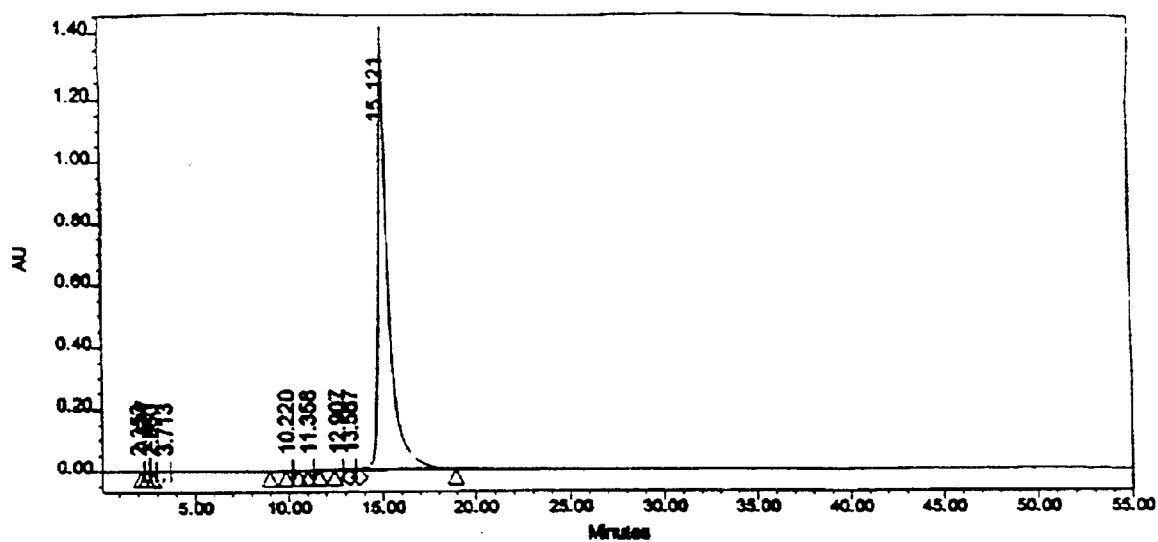
FIG. 9*c* is an analytical capillary gel electropherogram of the purified pool from the displacement of the phosphodiester illustrated in FIG. 9*a*.

The column that was regenerated after about 3 displacement runs in Example 2 was used to purify SEQ ID NO: 1 as a Phosphodiester. The general procedure illustrated in Example 1 was followed. High temperature anion-exchange analysis of the feed mixture for this separation is shown in FIG. 9a. The mixture contained several lower retained impurities which appear as shoulders on the main product peak. The displacement chromatogram resulting from the displacement of this oligonucleotide using amaranth is shown in FIG. 9B. Again, an effective separation was achieved resulting in a yield of 69.7% at 99% purity by the anion-exchange assay. The analytical capillary gel electropherogram of the purified pool of the purified phosphodiester is shown in FIG. 9c.

Example 4

Purification of a Phosphorothioate 20 mer Using Displacement Chromatography, SEQ ID NO: 2 (ISIS-2105) TTG CTT CCA TCT TCC TCG TC (P=S)

Figure 10:
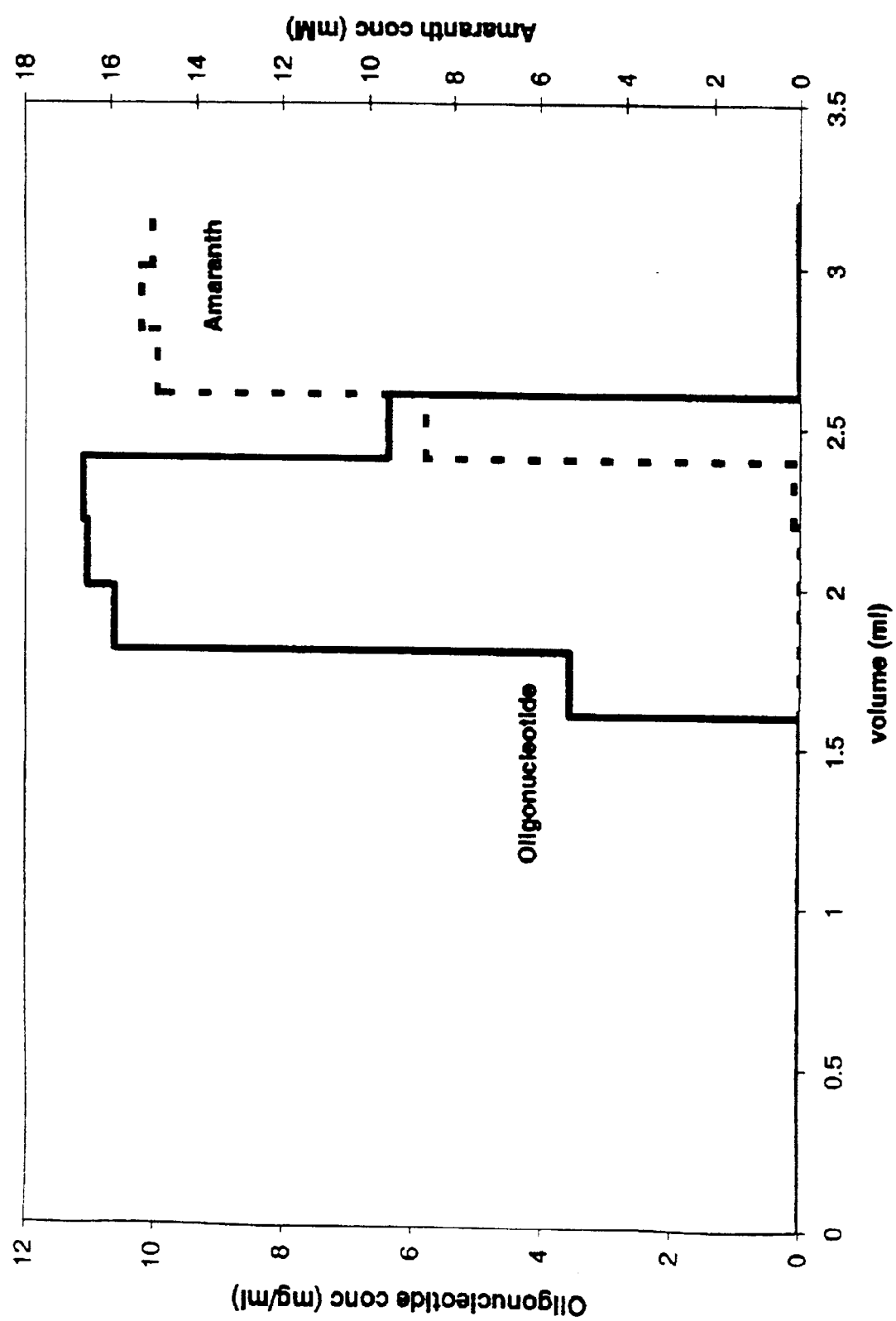
FIG. 10 is a displacement chromatogram for a phosphorothioate 20 mer SEQ ID NO. 2 (ISIS-2105) purified using displacement chromatography (Example 4).
Figure 11:
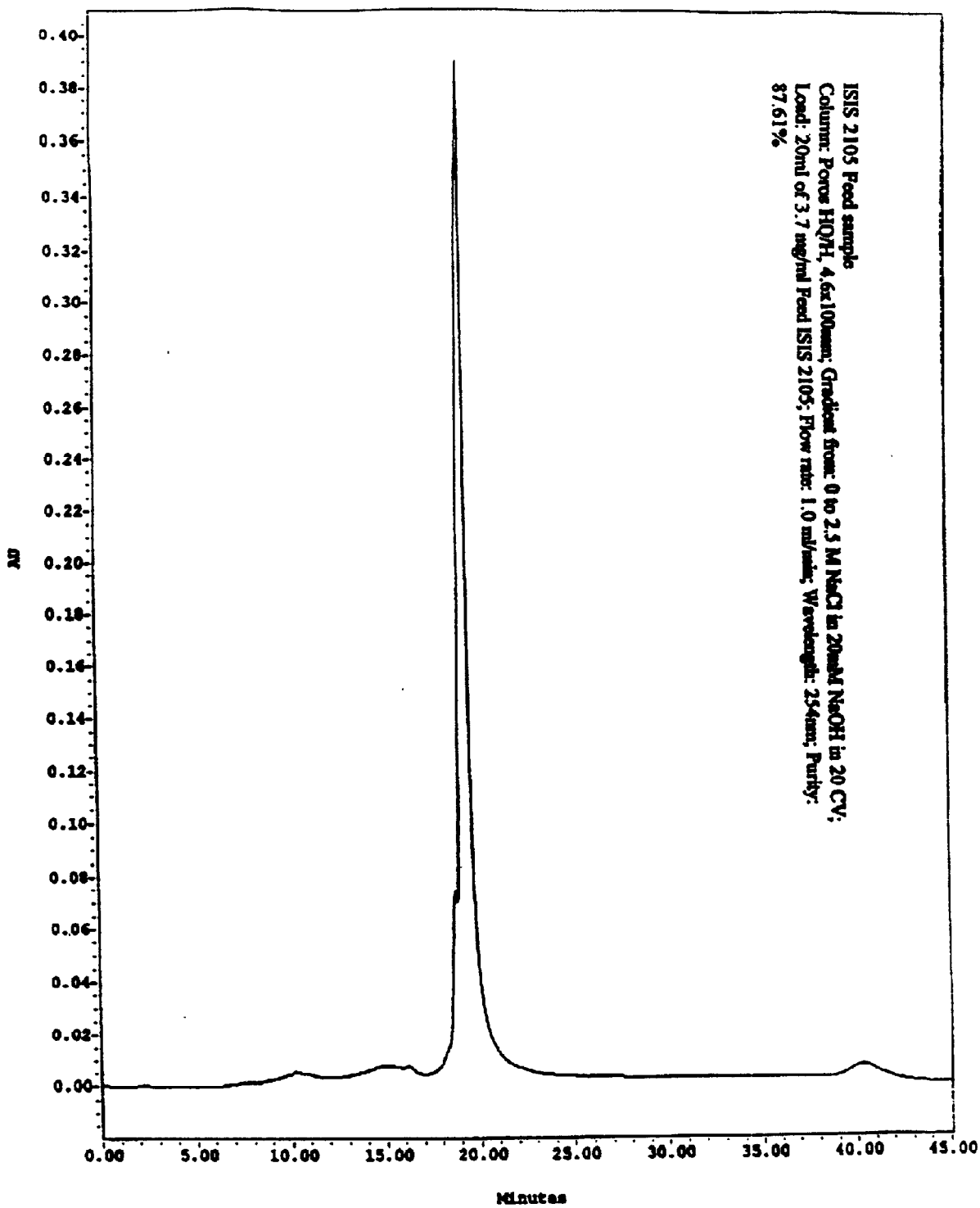
FIG. 11 is an anion-exchange chromatogram for the feed of the displacement chromatography shown in FIG. 10.
Figure 12:
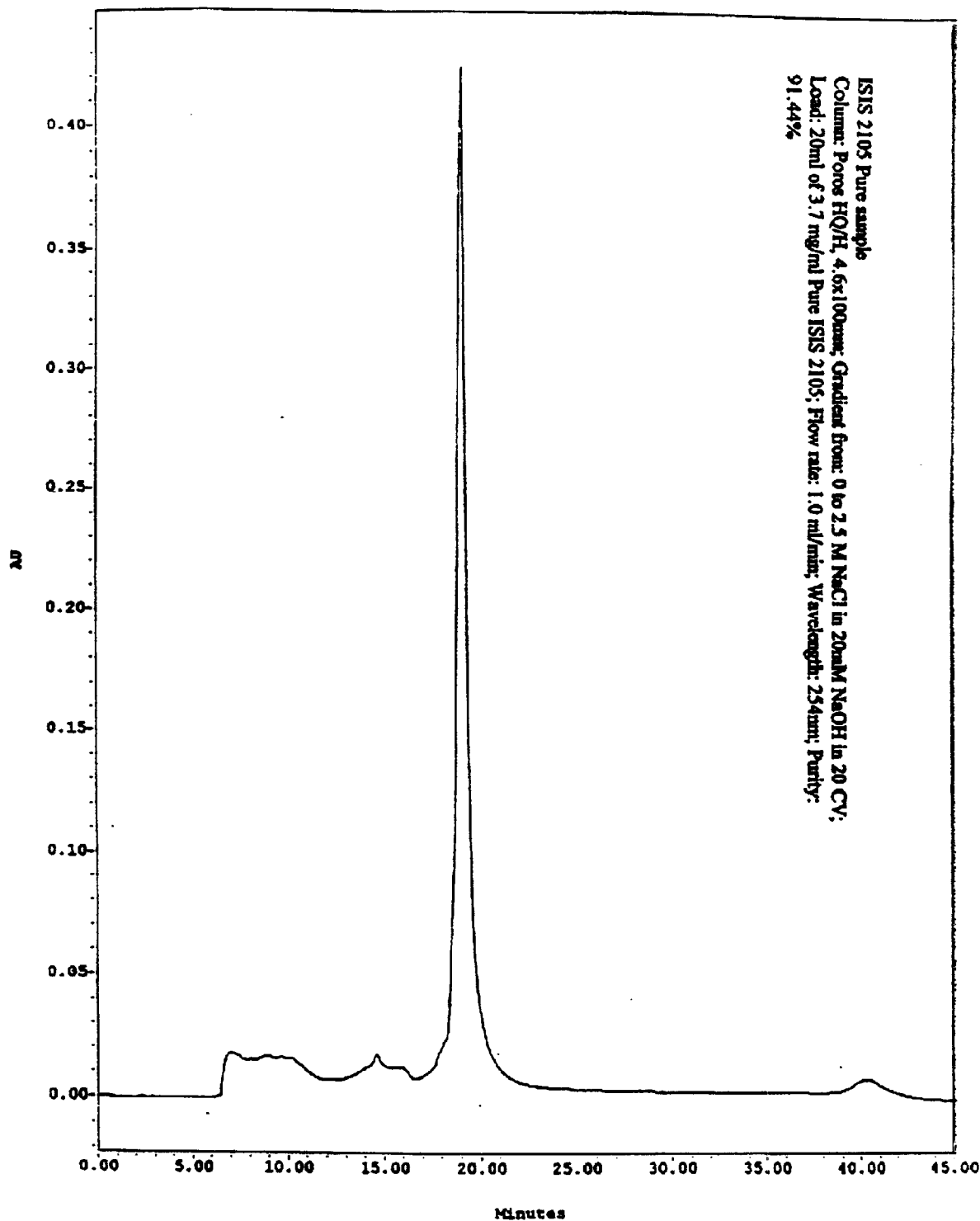
FIG. 12 is an anion-exchange chromatogram of the purified pool of the displacement chromatography shown in FIG. 10.

SEQ ID NO: 2, a phosphorothioate 20 mer, was purified by displacement chromatography using amaranth as the displacer. The chromatography was performed as per the procedure illustrated in Example 1 above. Column: 4.6×100 mm, Poros HQ/M; mobile phase: 20 mM NaOH/500 mM NaCl; loading: 10 mg phosphorothioate oligonucleotide; flow rate: 0.2 mL/min; feed purity=91.22%. FIG. 10 shows the displacement chromatogram. FIG. 11 shows the anion-exchange chromatogram and FIG. 12 shows the anion-exchange chromatogram of the purified pool.

While the invention has been particularly shown and described with reference to the preferred embodiments thereof, it will be understood by those skilled in the art that other changes in form and details may be made without departing from the spirit and scope of the invention.

What is claimed is:

1. A method for purifying an oligonucleotide comprising:
   (a) loading said oligonucleotide onto the stationary phase of an anion-exchange column; and
   (b) displacing said oligonucleotide from said stationary phase by an anionic displacer having a molecular weight of less than about 10,000, said anionic displacer having a higher affinity for said stationary phase than said oligonucleotide;
   wherein said anionic displacer is selected by a method comprising:
      (i) providing an anion exchange column comprising a stationary phase; said stationary phase comprising counter ions;
      (ii) contacting said oligonucleotide with said stationary phase;
      (iii) determining the affinity for said oligonucleotide for said stationary phase;
      (iv) contacting a displacer candidate with said stationary phase;
      (v) determining the affinity for said displacer candidate for said stationary phase;
      (vi) comparing the affinity of said displacer candidate with the affinity of said oligonucleotide; and
      (vii) selecting said displacer candidate for use as said anionic displacer in
   the purification of said oligonucleotide provided that said displacer candidate has a higher affinity than said oligonucleotide.

2. A method of selecting an anionic displacer for use in purifying an oligonucleotide utilizing an anion exchange column comprising:
   (a) providing an anion exchange column comprising a stationary phase, said stationary phase comprising counter ions;
   (b) contacting said oligonucleotide with said stationary phase;
   (c) determining the affinity for said oligonucleotide for said stationary phase;
   (d) contacting a displacer candidate with said stationary phase;
   (e) determining the affinity for said displacer candidate for said stationary phase;
   (f) comparing the affinity of said displacer candidate with the affinity of said oligonucleotide; and
   (g) selecting said displacer candidate for use as said anionic displacer in the purification of said oligonucleotide provided that said displacer candidate has a higher affinity than said oligonucleotide.

3. The method of claim 2 wherein the affinity for said stationary phase is determined by a method comprising:
   (a) determining the equilibrium constant (K) for the exchange reaction between said oligonucleotide or said displacer candidate and said counter ions of said anion exchange column;

(b) determining the partition ratio ($\Delta$) for said oligonucleotide or said displacer candidate;

(c) determining the characteristic charge ($\nu$) of said oligonucleotide or said displacer candidate; and (d) calculating said affinity ($\lambda$) according the equation $\lambda = (K/\Delta)^{1/\nu}$.

4. The method of claim 2 wherein the affinity for said stationary phase is determined by a method comprising:

(a) determining the equilibrium constant (K) for the exchange reaction between said oligonucleotide or said displacer candidate and said counter ions of said anion exchange column;

(b) determining the characteristic charge ($\nu$) of said oligonucleotide or said displacer candidate;

(c) plotting log K versus $\nu$;

(d) determining the slope of the log K versus $\nu$ plot; and (e) selecting said displacer candidate provided that the slope of the log K versus $\nu$ plot for said displacer candidate is greater than the slope of the log K versus $\nu$ plot for said oligonucleotide.

* * * * *